(12) United States Patent
Kirchengast et al.

(10) Patent No.: US 6,352,992 B1
(45) Date of Patent: Mar. 5, 2002

(54) ENDOTHELIN ANTAGONIST AND BETA RECEPTOR BLOCKING AGENT AS COMBINED PREPARATIONS

(75) Inventors: Michael Kirchengast; Klaus Münter, both of Mannheim (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/508,989

(22) PCT Filed: Sep. 10, 1998

(86) PCT No.: PCT/EP98/05772

§ 371 Date: Mar. 20, 2000

§ 102(e) Date: Mar. 20, 2000

(87) PCT Pub. No.: WO99/16444

PCT Pub. Date: Apr. 8, 1999

(30) Foreign Application Priority Data

Sep. 30, 1997 (DE) .......................................... 197 43 143

(51) Int. Cl.⁷ .............................................. A61K 31/505
(52) U.S. Cl. ....................................... 514/274; 544/316
(58) Field of Search ........................... 544/316; 514/274

(56) References Cited

FOREIGN PATENT DOCUMENTS

| EP | 617 001 | | 9/1994 |
|---|---|---|---|
| WO | WO 96/11914 | * | 4/1996 |
| WO | 96/19233 | | 6/1996 |
| WO | 96/22978 | | 8/1996 |
| WO | 98/09953 | | 3/1998 |
| WO | 98/24482 | | 6/1998 |
| WO | 98/27070 | | 6/1998 |

\* cited by examiner

*Primary Examiner*—Mukund J. Shah
*Assistant Examiner*—Hong Liu
(74) *Attorney, Agent, or Firm*—Keil & Weinkauf

(57) ABSTRACT

A combination of endothelin antagonists and beta-receptor blockers is described. The combination is suitable for controlling diseases.

4 Claims, No Drawings

ENDOTHELIN ANTAGONIST AND BETA RECEPTOR BLOCKING AGENT AS COMBINED PREPARATIONS

The present invention relates to novel pharmaceutical combination preparations which are suitable for treating disorders based on vasoconstriction and which comprise a beta-receptor blocker and an endothelin antagonist.

Combination preparations which are suitable for treating disorders based on vasoconstriction and which comprise a beta-receptor blocker and an endothelin antagonist have already been disclosed (WO 92/13545). However, the activity of these active compound combinations is unsatisfactory.

Combinations having improved properties have now been found.

The present invention provides a combination of an endothelin antagonist of the formula I

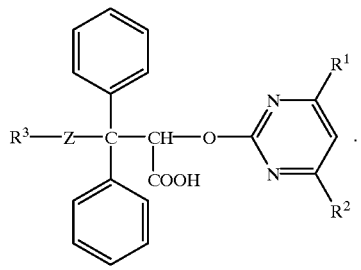

I in which the substituents are as defined below:

$R^1$ is $C_1$–$C_4$-alkyl, $C_1$–$C_4$-alkoxy;

$R^2$ is $C_1$–$C_4$-alkyl, $C_1$–$C_4$-alkoxy;

$R^3$ is $C_1$–$C_8$-alkyl, which may be substituted by a phenyl radical which for its part may be substituted by one or two $C_{1-4}$-alko-xy radicals, z is oxygen or a single bond, and a beta-receptor blocker. Preferred endothelin antagonists are those compounds of the formula I where the substituents are as defined below:

$R^1$: $C_1$–$C_2$-alkyl, $C_1$–$C_2$-alkoxy $R^2$: $C_1$–$C_2$-alkyl, $C_1$–$C_2$-alkoxy $R^3$ is $C_1$–$C_2$-alkyl which may be substituted by a phenyl radical whch for its part may be substituted by one or two $C_1$-2-alkoxy radicals, Z is oxygen or a single bond.

Particularly suitable endothelin antagonists are the compounds:

A.

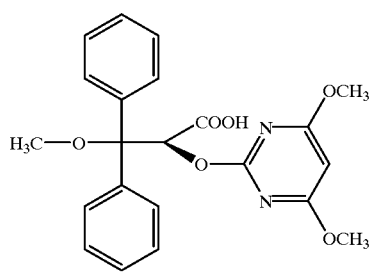

-continued

B.

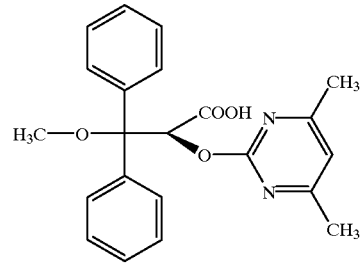

C.

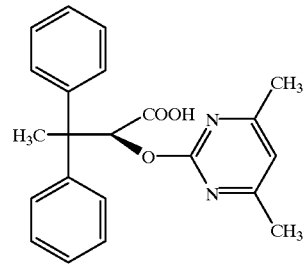

D.

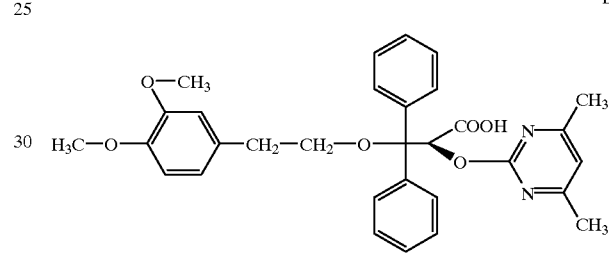

Suitable beta-receptor blockers are, in particular, acebutolol, alprenolol, atenolol, metoprolol, bupranolol, penbutolol, propranolol, esmolol, bisoprolol, carazolol, talinolol, mepindolol, sotalol, metipranolol, pindolol, carteolol, tetratolol, celiprolol, nadolol, oxprenolol and bopindolol. In particular, carvedilol and bucindolol may be mentioned.

The combination of a β-blocker with an inhibitor of the ET-system can be used as a composition for treating diseases which are based on vasoconstriction or associated with pathological vasoconstriction. Examples are: all forms of high blood pressure (including pulmonary hypertension), coronary heart diseases, cardiac insufficiency, renal and myocardiac ischemia, acute and chronic renal insufficiency.

Diseases which are associated with vasoconstriction or other biological effects of endothelin and/or angiotensin II are, in particular, the control and/or prevention of coronary disorders, cardiovascular disorders, such as hypertension, cardiac insufficiency, ischemia (in heart, brain, gastrointestinal tract, liver and/or kidney) or vasospasms. Other examples of diseases which can be treated are renal and myocardiac ischemia, renal insuffiency, dialysis, subarachnoidal haemorrhage, Raynaud's syndrome, portal high pressure and pulmonary high pressure and also the treatment of gastric and duodenal ulcers and of stasis ulcer where vasoconstriction is involved. Finally, in asthma patients the concentration of endothelin in the bronchial discharge is increased. In migraine attacks, too, increased endothelin levels in the blood plasma are observed. The combination can therefore also be used in these cases.

When the combination according to the invention is administered, there is a significant increase of the antihypertensive properties and the duration of action compared with the individual substances, and this effect is superadditive. Accordingly, the doses of the individual active compounds can be reduced considerably. Thus, there is a lower risk of adverse effects during administration.

The weight ratio of β-receptor blocker to endothelin antagonists is usually in the range from 50:1 to 1:500, preferably from 10:1 to 1:100 and in particular from 2:1 to 1:50.

The combinations according to the invention are generally administered orally, for example in the form of uncoated, lacquered or sugar-coated tablets, hard and soft gelatin capsules, solutions, emulsions or suspensions. However, administration can also take place rectally, for example in the form of suppositories, or parenterally, for example in the form of solutions for injection. Administration of the active compound can take place in the form of products which contain both active compounds together, such as tablets or capsules, or separately as ad hoc combination of single substances, which can be administered concurrently or sequentially.

To produce uncoated, lacquered or sugar-coated tablets and hard gelatin capsules, a combination according to the invention can be processed with pharmaceutically inert inorganic or organic excipients. Excipients of these types which can be used for uncoated and sugar-coated tablets and hard gelatin capsules are lactose, corn starch or derivatives thereof, talc, stearic acid or salts thereof. Suitable excipients for soft gelatin capsules are vegetable oils, waxes, fats, semisolid and liquid polyols.

Suitable excipients for producing solutions and syrups are, for example, water, polyols, sucrose, invert sugar, glucose and the like. Suitable excipients for solutions for injection are water, alcohols, polyols, glycerol, vegetable oils. Suitable excipients for suppositories are natural or hydrogenated oils, waxes, fats, semiliquid or liquid polyols and the like.

The pharmaceutical preparations may additionally comprise preservatives, solubilizers, stabilizers. Wetting agents, emulsifiers, sweeteners, colorants, flavorings. Salts to alter the osmotic pressure, buffers, coating agents and/or antioxidants.

The unexpected advantageous properties of the combinations according to the invention are demonstrated by the tests below:

In a crossover design, the test substance was administered orally as a capsule to chronically instrumented male beagle dogs (approx 14 kg). The capsule either contained nothing (control N=5), compound A (10 mg/kg, N=10), bucindolol (0.1 mg/kg; N=5) or the combination bucindolol + compound A (0.1+10 mg/kg; N=5). In between the individual administrations, a washing phase of at least one week was observed. The systolic and the diastolic blood pressure were measured using a Statham Transducer P 23 Db, from which the mean arterial blood pressure was calculated. The blood pressure was recorded for 6 h ($MI^2$, Modular Instrumente, USA).

Table 1 shows that the blood pressure in the control group and in the group treated with bucindolol does not decrease. With compound A, a slight reduction in blood pressure can be observed. The combination of bucindolol with the ET antagonist compound A (0.1+10 mg/kg) resulted in a considerable lowering of the blood pressure.

Table 1:

Development of the mean arterial blood pressure (mmHg, change with respect to the initial value) in normotensive awake dogs after oral administration of different substances, what is shown are the mean values

|  | N | Initial value | 1h | 2h | 3h | 4h | 5h | 6h |
|---|---|---|---|---|---|---|---|---|
| Placebo | 10 | 103 | 3 | 2 | 2 | 1 | 1 | 1 |
| Compound A 10 mg/kg | 10 | 99.6 | −5.9 | −8.9 | −9.0 | −9.1 | −8.4 | −8.2 |
| Bucindolol 0.1 mg/kg | 5 | 100.4 | −0.8 | −3.8 | −3.4 | −3.8 | −3.8 | −1.4 |
| Combination A + Bu 10 + 0.1 mg/kg | 5 | 100.8 | −8.8 | −15.2 | −17 | −15.6 | −13.4 | −11.8 |

The following examples illustrate the invention.

EXAMPLE 1

Lacquered tablets of the following composition were prepared:

| | |
|---|---|
| Compound A | 100.0 mg |
| Bucindolol | 10.0 mg |
| Anhydrous lactose | 30.0 mg |
| Microcrystalline cellulose | 30.0 mg |
| Polyvinylpyrrolidone | 20.0 mg |
| Magnesium stearate | 5.0 mg |
| Polyethylene glycol 6000 | 0.8 mg |
| Iron oxide yellow | 1.2 mg |
| Titanium dioxide | 0.3 mg |
| Talc | 0.7 mg |

Compound A, bucindolol, the lactose, the gellulose and the polyvinylpyrrolidone are wet-granulated and dried. The screened granules are mixed with the magnesium stearate, and the ready-to-be-compressed mixture is compressed to oval tablet cores each weighing 190.0 mg. The cores are then lacquer-coated until the lacquer-coated tablets have reached a final weight of 200 mg.

EXAMPLE 2

Preparation of hard gelatin capsules of the following composition:

| | |
|---|---|
| Compound A | 100.0 mg |
| Bucindolol | 30.0 mg |
| Cryst. lactose | 18.0 mg |
| Polyvinylpyrrolidone | 15.0 mg |
| Microcrystalline cellulose | 17.5 mg |
| Sodium carboxymethyl starch | 10.0 mg |
| Talc | 9.0 mg |
| Magnesium stearate | 3.0 mg |

The first five components are wet-granulated and dried. The granules are mixed with the sodium carboxymethyl starch, the talc and the magnesium stearate, and the mixture is packed into size 1 hard gelatin capsules.

We claim:

1. A combination of an endothelin antagonist of the formula I

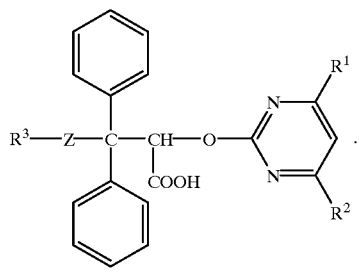

in which the substituents are as defined below:

$R^1$ is $C_1$–$C_4$-alkyl, $C_1$–$C_4$-alkoxy;

$R^2$ is $C_1$–$C_4$-alkyl, $C_1$–$C_4$-alkoxy;

$R^3$ is $C_1$–$C_8$-alkyl which may be substituted by a phenyl radical which for its part may be substituted by one or two $C_{1-4}$-alkoxy radicals, Z is oxygen or a single bond, and a beta-receptor blocker.

2. A pharmaceutical preparation, comprising a combination as claimed in claim 1.

3. A process for preparing a pharmaceutical preparation, which comprises bringing a mixture of a beta-receptor blocker and an endothelin antagonist as claimed in claim 1 into a pharmaceutical administration form.

4. A pharmaceutical preparation comprising a beta-receptor blocker and an endothelin antagonist as claimed in claim 1, for simultaneous, separate or successive use in the treatment of diseases.

* * * * *